(12) United States Patent
Slautterback et al.

(10) Patent No.: US 6,394,971 B1
(45) Date of Patent: May 28, 2002

(54) ANKLE BRACE AND SUPPORT AND METHOD

(75) Inventors: Ernest Gerald Slautterback, Coral Springs; Rhonda M. Machin, Weston, both of FL (US)

(73) Assignee: FLA Orthopedics, Inc., Miramar, FL (US)

( * ) Notice: Subject to any disclaimer, the term of this patent is extended or adjusted under 35 U.S.C. 154(b) by 0 days.

(21) Appl. No.: 09/772,441

(22) Filed: Jan. 30, 2001

(51) Int. Cl.[7] .................................................. A61F 5/00
(52) U.S. Cl. ............................ 602/27; 602/23; 602/60; 602/65
(58) Field of Search .......................... 602/5, 23, 27–29, 602/60–63, 65

(56) References Cited

U.S. PATENT DOCUMENTS

| | | |
|---|---|---|
| 3,073,305 A | 1/1963 | Biggs |
| 4,280,488 A | 7/1981 | Polsky |
| 4,724,847 A | 2/1988 | Inglesius |
| 5,069,202 A | 12/1991 | Prock |
| 5,330,419 A * | 7/1994 | Toronto et al. ................ 602/27 |
| 5,472,414 A | 12/1995 | Detty |
| 5,795,316 A * | 8/1998 | Gaylord ....................... 602/27 |
| 5,853,380 A | 12/1998 | Miller |
| 5,899,872 A | 5/1999 | Gilmore |
| 6,024,712 A | 2/2000 | Inglesias |
| 6,155,997 A * | 12/2000 | Castro ......................... 602/27 |

* cited by examiner

Primary Examiner—Jeanette Chapman
Assistant Examiner—Lalita M Hamilton

(57) ABSTRACT

Disclosed is an ankle support which includes a low temperature, formable plastic, closed-cell foam sewn to a soft orthopedic appliance to provide the desired rigidity and conformability, and a method of making the same. The closed-cell foam is in a skeletal configuration comprising a relatively wide collar for encircling the leg of a wearer and supporting a plurality of relatively narrow elongated stiffeners depending therefrom substantially normal thereto. At least one of the stiffeners terminates in a J-shape. In producing the new brace, a polyolefin foam is laminated with nylon fabric on both of its surfaces. The laminated foam is then cut to desired blank shape. This blank is then sewn to the fabric of the soft brace, also in flat blank shape. The soft brace is then sewn into its sock configuration. The combined foam sheet and attached soft brace blanks in a sock configuration are then mounted upon a male die and subjected to low temperature heat and pressure forming. The molding step transforms the previously soft foam into a semi-rigid skeletal "shell" that extends around but does not substantially completely encase the ankle. The soft appliance provides the basic support, while the skeletal shell provides tailored localized flexible stiffening.

10 Claims, 9 Drawing Sheets

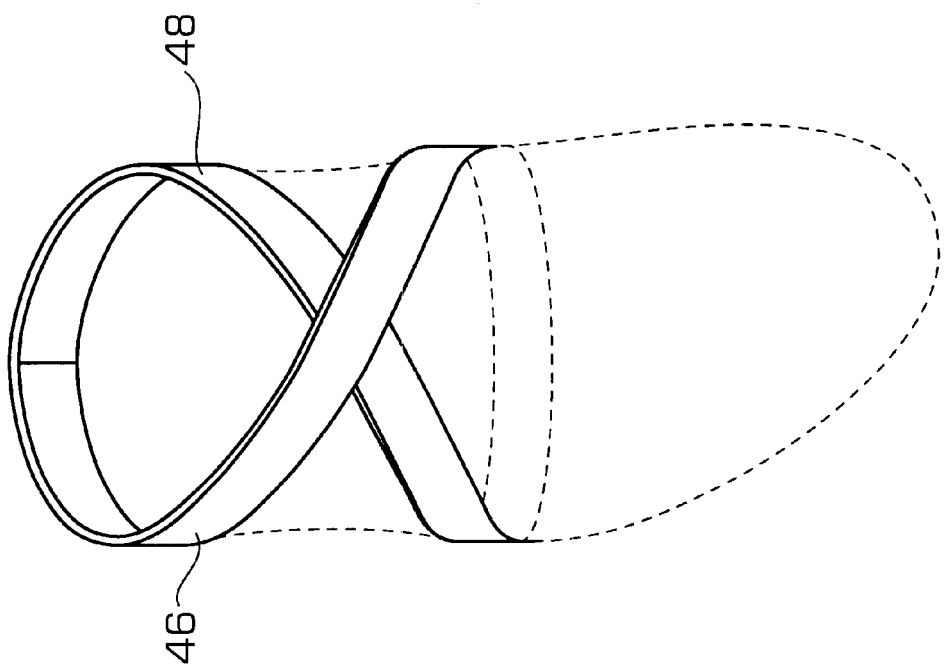
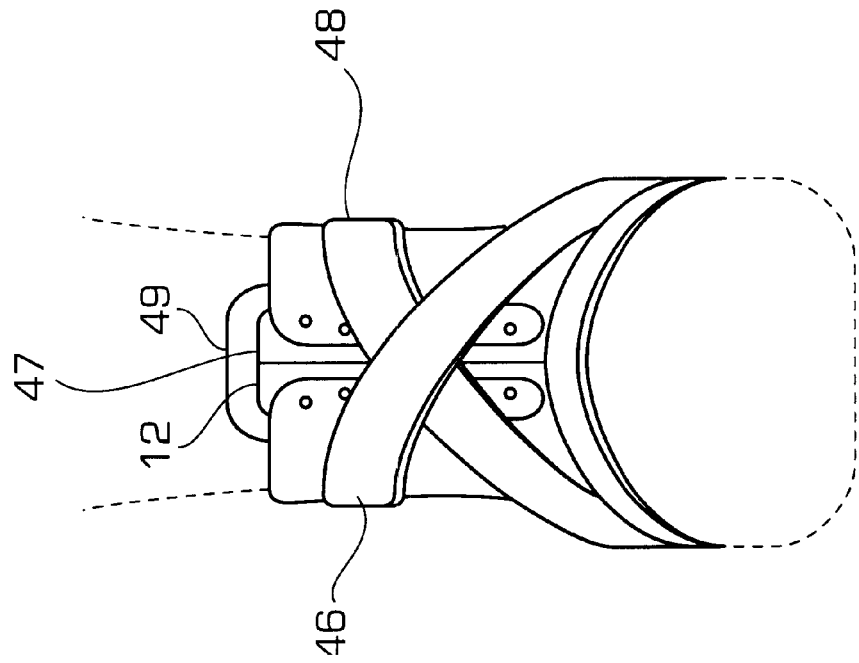

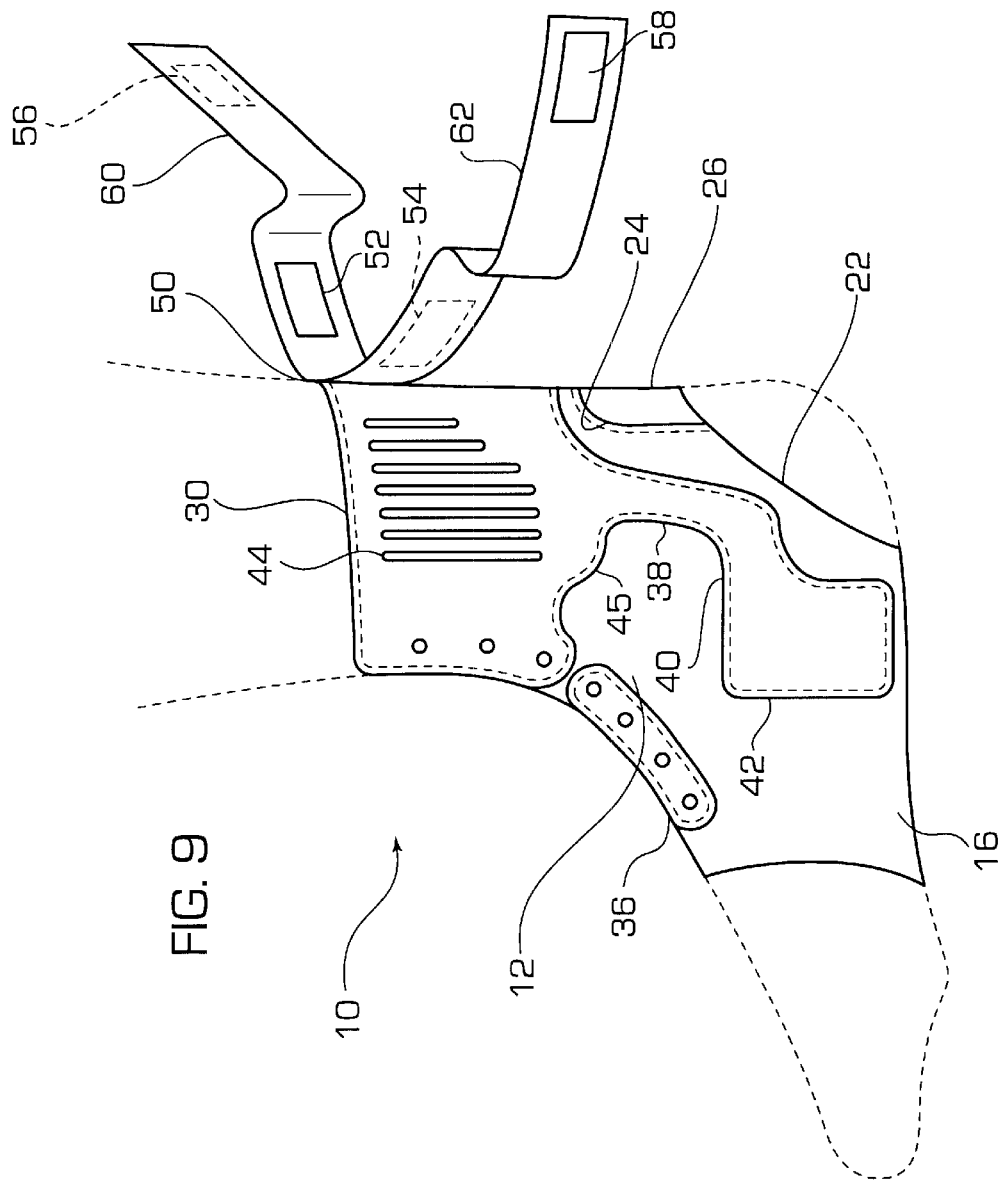

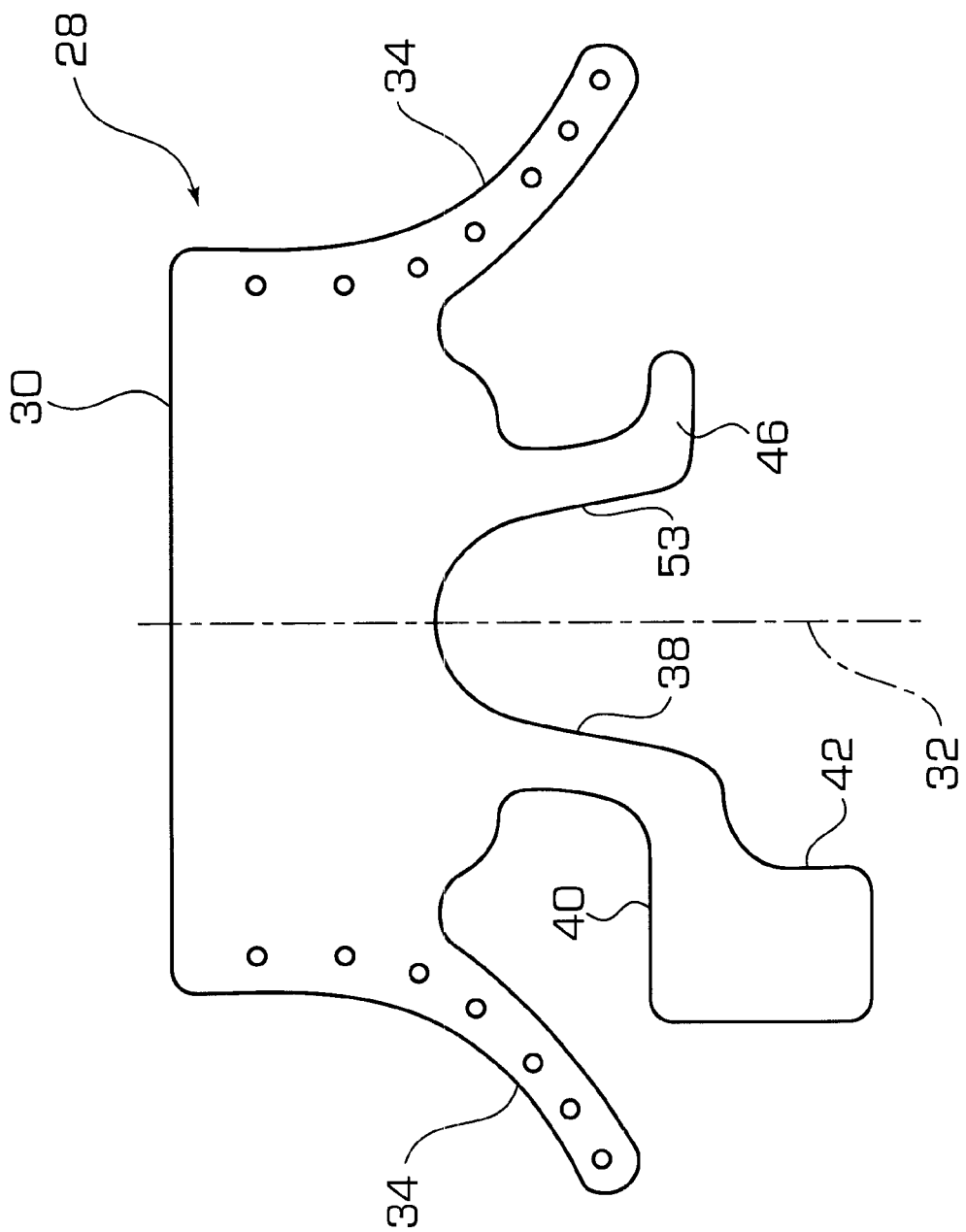

ANKLE BRACE AND SUPPORT AND METHOD

The present invention relates generally to orthopedic devices and more particularly to improved ankle braces and supports and the method of their manufacture.

BACKGROUND

The present day market for orthopedic devices offers a number of different ankle products of varying types. The product types vary in many respects and particularly in the amount or degree of stabilization provided. Ankle products range from simple compressive elastic sleeves to rigid, plastic immobilizing braces. The most common ankle product is a lace-up style brace that is indicated for both rehabilitative and preventative use. These braces help medially and laterally stabilize the ankle joint to prevent inversion and eversion (twisting) of the ankle, while still allowing for functional dorsi and plantar flexion. This type of stabilization is typically achieved in traditional ankle braces with metal, plastic or spring type stays, boning or inserts. By stabilizing the medial and lateral sides of the ankle joint, the brace is indicated to prevent further injury and treat strains and 1st, $2^{nd}$, and 3rd degree ankle sprains. The brace is also employed as a preventative prophylactic to help avoid ankle sprains during activity. Historically, ankle braces with rigid stays or inserts have been utilized for these indications.

However, metal or plastic stays or inserts can dig into the tender tendons that these braces were designed to protect. Additionally, rigid stays and inserts cannot conform to the unique ankle shape to give the intimate support and stabilization necessary.

A sample of prior art patents illustrating some of these devices includes the following:

U.S. Pat. No. 4,724,847, issued Feb. 16, 1988, to Ronald E. Nelson, shows a soft orthopedic ankle support that has a plurality of pockets. Rigid stay members are inserted into the pockets to form a rigid structure that surrounds and immobilizes the ankle. U.S. Pat. No. 4,280,488 shows a similar stay stiffened soft orthopedic ankle support.

U.S. Pat. No. 5,853,380, issued to John J. Miller, Dec. 29, 1998, shows an ankle and foot orthopedic device wherein inner and outer layers of soft plastic materials are assembled in a sandwich around a rigid copolymer plastic stay which cradles the ankle and foot. In fabricating the device the inner layer of plastic material is heated and then wrapped around a plaster mold. The mold is equipped with suction by which the sheet can be sucked down to conform to the shape of the mold. The outer surface of the inner layer is then abraded and the stay is placed over the abraded surface. Once the stay is in place, adhesive is sprayed over the entire exposed surface of the inner layer and the stay. Finally the outer layer of plastic is heated and wrapped around the inner layer and stay, sucked down by the vacuum to conform to the shape of the mold, cooled, and trimmed to shape.

U.S. Pat. No. 5,899,872, issued May 4, 1999 to Robert F. Gilmore, describes a foot and ankle support which includes a soft appliance, somewhat elastic, boot element. The somewhat elastic boot element is tightened by means of spaced flaps secured by hook and loop fasteners. Conventional straps encircle the boot. In another embodiment a rigid brace is applied over the boot and affixed by one or more of the straps.

U.S. Pat. No. 5,069,202, issued Dec. 3, 1991, to Steven D. Prock, shows a stirrup type of ankle brace which includes a foot shell having rigid vertical and horizontal portions hingedly connected. This shell is held onto the ankle and foot of the wearer by straps.

U.S. Pat. No. 3,073,305, issued Jan. 15, 1963, to Ernest R. Biggs, et al., shows an ankle brace including a fabric sleeve fitting along the foot and ankle with a strap arrangement spiraling up the leg, and essentially vertical stays inserted in pockets along the leg part of the sleeve.

U.S. Pat. No. 5,472,414, issued Dec. 5, 1995, to Michael K. Detty, describes a one-size-fits-all ankle brace comprising a base of plush fabric covered neoprene having an upper ankle surrounding portion and an upper pair of mounting straps, and a lower foot surrounding portion with a lower pair of mounting straps. The base member is folded into an ankle and foot encasing position with the upper straps wrapped around the ankle and the leg just above the ankle, and the lower straps wrapped around the ankle arch and instep. Hook and loop fasteners hold the straps in position.

U.S. Pat. No. 6,024,712, issued Feb. 15, 2000, to Joseph M. Inglesias, describes an ankle brace using an inner fabric support which extends around the ankle. An outer plastic exo-support is injection molded into the fabric support to resist motion of the injured ankle in undesired directions. The exo-support has side members extending upwardly from a base to provide stirrup like support.

While the aforementioned prior art ankle braces may be generally suitable for their intended purposes, they nevertheless leave something to be desired from the standpoints of accommodating various sized ankles while supplying sufficient customized support, and ease and economy of manufacture. Thus, a need exists for an ankle brace which fits a range of sizes, which is simple in construction and manufacture, easy to use, and which has means to adjust and customize the support applied by the brace without producing the aforementioned adverse effects of metal or other rigid stays.

OBJECTS OF THE INVENTION

It is a primary object of the invention to eliminate the above described problems and shortcomings of the prior art.

It is another object of the invention to provide an improved ankle support comprising a unique combination of low temperature formable plastic foam and a sewn orthopedic soft appliance, which provides ease of economic manufacture.

It is yet another object of the invention to provide an improved methodology for manufacturing an improved ankle support which is fabricated from a combination of low temperature formable plastic foam and a sewn orthopedic soft appliance.

It is a further object of the invention to provide a combination of a sewn soft ankle brace with a contoured semi-rigid support shell of molded foam to produce a snug fitting orthopedic device which gives improved stabilization of the ankle joint.

It is yet a further object of the invention to provide such a combination orthopedic device in which the shell is molded with a unique shape or configuration that flexes around the ankle to provide medial and lateral stabilization without digging into the skin.

It is another object of the invention to provide such an orthopedic wherein a uniquely J-shaped portion of the shell is supported from a collar on the shell and sewn to an inner sock or sleeve to cradle and support the ankle joint without creating pressure points on the sensitive ankle malleoli.

It is yet another object of the invention to provide an orthopedic of the foregoing type wherein the shell has a leg encircling collar which carries depending stiffeners and has a width sufficient to provide cantilever type tensioning of one or more of such stiffeners against an extremity of a wearer.

It is yet another object of the invention to provide an orthopedic of the foregoing type wherein the shell is of an asymmetric shape to even further avoid the creation of pressure points on the ankle malleoli.

SUMMARY OF THE INVENTION

The present invention is directed to a unique incorporation of the technology of low temperature, formable plastic foam with sewn fabrics in the manufacture of improved orthopedic appliances. Particularly the invention is directed to integration of these two approaches for use in ankle and knee braces.

In sewn orthopedic soft appliances and braces the most common means to obtain the rigidity necessary to stabilize the injured joint is by using metal or plastic strips called "stays". These stays are actually sewn to the product to prevent movement of the joint. However, in some product applications stays simply cannot conform to the anatomy of the patient to provide the necessary support and immobilization. Additionally, in some cases, stays may be too rigid, too uncomfortable or "dig" into the skin.

Low temperature, formable plastic, closed-cell polyolefin foams, such as the foam sold under the trademark VOLARA, have been used as splinting materials in a number of orthopedic products. VOLARA foam is formable by a variety of techniques and is readily available.

According to the present invention low temperature, formable plastic, closed-cell foams are sewn to a soft orthopedic appliance to obtain the necessary rigidity and conformability without stays. This provides a more comfortable, better fitting product for greater conformability and immobilization. The product is to be contrasted with products which incorporate a soft appliance in an outer shell in such a manner as to detract from or eliminate the advantages provided by a soft appliance. One example of such a prior arrangement uses injection molding to incorporate a soft appliance into a hard outer shell which encompasses a substantial area of the skin of the wearer. The inventive combination of the technologies of formable foams with traditional sewn orthopedic products yields unique products having improved product function.

In one particular embodiment of the invention, low temperature, formable plastic, closed-cell foam is used in combination with a traditional sewn product to obtain better stabilization of the ankle. A semi-rigid formed foam "shell" of a unique shape provides the necessary medial and lateral stabilization. This is to be contrasted with products which include a relatively rigid boot encasing the bottom of the foot.

In producing the new brace, a polyolefin foam, such as VOLARA, is laminated with nylon or the like fabric on both of its surfaces. The thus laminated foam is then cut to desired blank shape by standard material clickers. This blank of flat foam laminate is then sewn to the soft, nylon or nylon like fabric of the soft brace, also in flat blank shape. The combined foam sheet and attached soft brace blanks are then subjected to heat and pressure forming after the sewing is complete. The molding step transforms the previously soft foam into a semi-rigid skeletal "shell" that extends around but does not substantially completely encase the ankle. The soft appliance provides the basic support, while the skeletal shell provides tailored localized flexible stiffening. This approach and its associated production methodology is to be contrasted with more elaborate and costly known techniques.

The combination of the soft ankle brace with a contoured semi-rigid support shell gives a contoured, snug fit for much better stabilization of the ankle joint. The shell is molded with a unique skeletal shape or configuration that flexes around the ankle to provide medial and lateral stabilization without digging into the skin. The foundation for the support provided by the skeletal elements of the shell is an adjustable circumferential collar secured around the leg above the ankle joint. From this collar depend a pair of generally diametrically opposite medial and lateral fingers or stiffeners which terminate in one or two unique J-shaped ends. The collar and fingers are sewn to the soft brace to provide a unique cradling and support to the ankle joint without creating pressure points on the sensitive ankle malleoli. Aside from the foundational collar the shell does not provide extensive area coverage. It does provide tailored stiffening in selected locations, thereby enhancing the basic support provided by the soft appliance. The collar has a width sufficient to provide cantilever type tensioning of one or more of the fingers or stiffeners against the extremity of the wearer.

With this product the fragile or damaged ankle tendons and the sensitive ankle malicoli are protected from further impact or shock. Using low temperature, formable plastic, closed-cell foam, such as VOLARA, as the support shell in the new configuration replaces the need for a metal stay or plastic inserts. The molded foam is sufficient to stabilize the ankle joint but is much less rigid than previously used steel or aluminum or rigid plastics. This gives a more conforming fit, provides a layer of molded foam protection, and eliminates the use of rigid metal around the sensitive tendons and malleoli.

In one preferred embodiment of the improved ankle brace there is provided a soft fabric sock-like sleeve having a cutaway open heel and toe. This provides basic soft sewn appliance support to the joint to be protected. A flat sheet of a compressible heat formable closed cell polyolefin, such as VOLARA, is sandwiched between surface sheets of woven fabric, such as nylon or the like. This soft laminated composite material is then cut to a predetermined pattern to form a blank having a flat skeletal configuration. The configuration is designed so that when it is shaped into a generally cylindrical form it will provide an above the ankle leg encircling collar at its top. The width of the collar is such as to form a foundation for supporting the skeletal elements of the shell, including elongated depending stiffeners. It is a feature of the invention that the collar provides cantilever type support for depending stiffeners that are relatively narrow in width. However, the stiffeners are provided with the desired semi-rigidity by increasing their effective cross section. Thus the desired flexural strength may be provided by an increase of the thickness or by the use of stiffening ridges or the like. In certain embodiments the stiffeners may be further adjustably supported by straps. This permits individual customization of degree of support afforded by the stiffeners.

The open heel and toe, sock-like soft brace material, also in its flat blank configuration, is then sewn to the skeletal shell blank in a predetermined stitching pattern. The collar of the shell blank is sewn to the upper or above the ankle portion of the soft brace fabric so as to substantially encircle it when the soft brace is in its sock or sleeve form. Depending from this collar are substantially vertical fingers which terminate in one or two J shaped arms disposed to extend down the back side of the ankle joint and thence forwardly beneath the ankle. These fingers and J-shaped arms are sewn to portions of the flat sock or sleeve blank so as ultimately to be disposed on opposite sides thereof. A padded tongue is tacked to one of two edges of the sleeve blank which are to be sewn together.

The flat sleeve blank with the attached tongue is then curved from its flat blank configuration into its sock or sleeve form, and seamed to itself to hold that shape. The seamed sleeve and its surrounding shell blank are then mounted on a male mold and heat and pressure applied in the molding step.

The shell blank is transformed by the molding from its soft foam state into a resilient semi-rigid skeletal state. In this form and configuration it possesses resilience, flexibility, and semi-rigidity. The formed shell is provided with lace apertures, eyelets or hooks for speed lacing, in approximately the same positions as these would be found in a high topped shoe. Lacing through these apertures, or the like, provides adjustability in the collar from which the stiffening fingers depend.

A pair of straps are affixed to the rear of the shell collar for forming a figure 8 support over the combined outer surfaces of the shell and sock. The strap ends are fastened behind the collar of the shell by hook and loop fasteners. The straps pass over and beneath the sock and provide an adjustability of tension which is not found in stirrup type braces. The straps preferably engage the outer surfaces of the stiffeners to provide an added element of support.

BRIEF DESCRIPTION OF THE DRAWINGS

Further objects and advantages of the present invention will become apparent as the following description of illustrative embodiments proceeds, taken in conjunction with the accompanying drawings in which:

FIG. 7 is a front elevation showing the unlaced brace on a foot of a wearer, shown in phantom, with the fastening straps in a secured position.

FIG. 8 is a top or plan view showing the figure 8 configuration of the fastening straps in relation to a wearer's foot, shown in phantom.

FIG. 9 is a side elevation similar to FIG. 1, showing another embodiment of the invention.

FIG. 10 is a side elevation similar to FIG. 1, illustrating yet another embodiment of the invention.

DETAILED DESCRIPTION OF A PREFERRED EMBODIMENT

Figure 1:
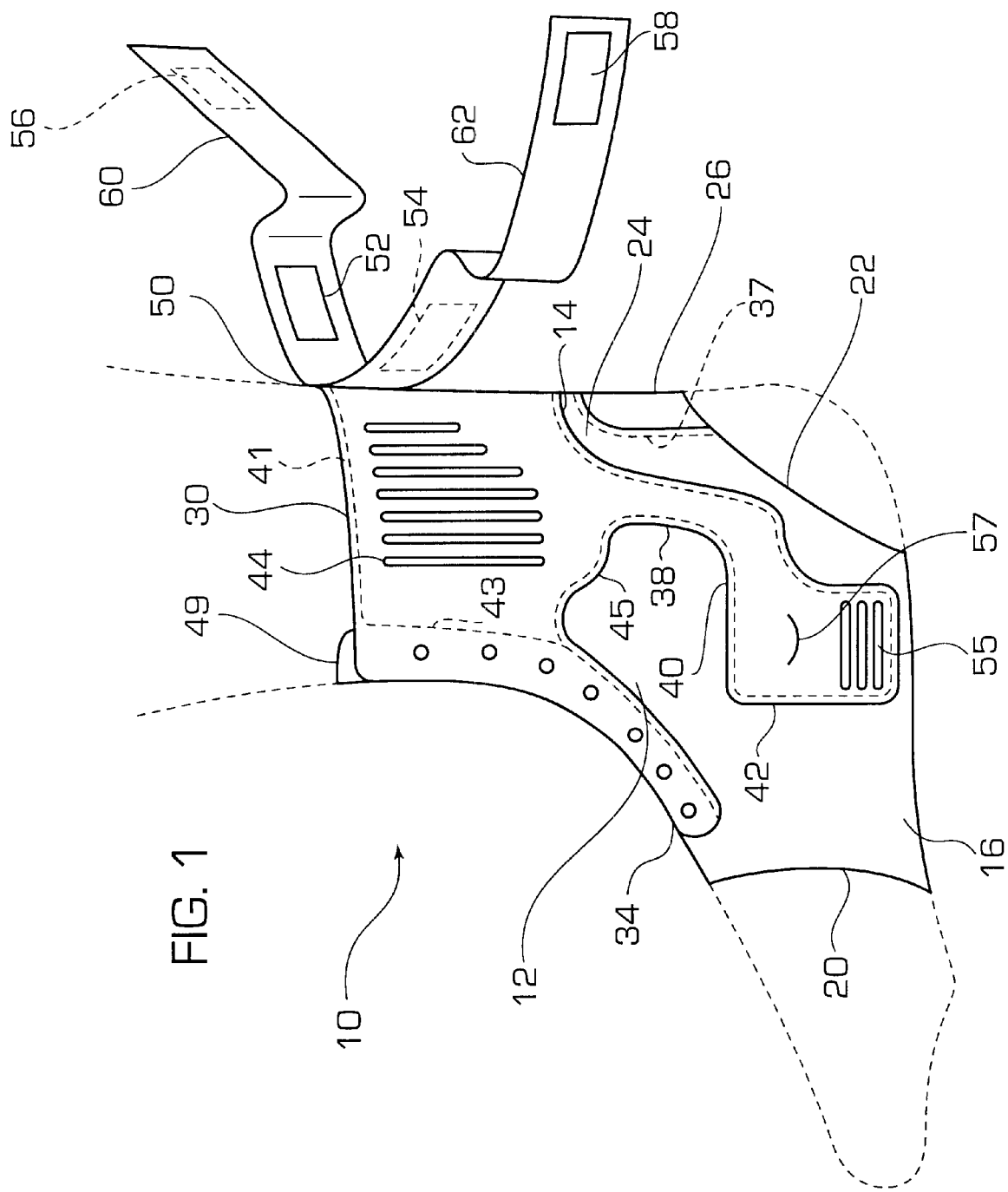
FIG. 1 shows a left side elevation of one preferred embodiment of an ankle support constructed according to the invention on the left ankle and foot of a wearer, shown in phantom. The support is illustrated prior to lacing and securement of the support straps.

Referring to FIG. 1, there is seen a left side elevation of one preferred embodiment of an ankle support or brace 10 constructed according to the invention. The ankle support is illustrated as worn on the left ankle and foot of a wearer, shown in phantom. The support embodies a new combination of a sewn soft ankle brace with a contoured semi-rigid support shell of low temperature molded foam. The support includes a woven fabric sleeve or sock 12 formed of nylon or the like fabric. Such a sleeve is shown in side elevation in FIG. 2, exploded from its combination with an outer shell. The same sleeve is illustrated in front elevation in FIG. 3.

Extending upward from the edge 22 of the open heel cut away is a further cut away defined by the edge 21. An elastic fabric insert 26 is sewn to the edge 21 of the further heel cut away at 24 to cover this opening. This improves conformability and enhances the range of comfortable movement of the foot and ankle.

Extending upward from the open heel cut away 22 is a further cut away 24. An elastic fabric insert 26 is sewn to the edge of the heel cut away 24 to cover this opening. This improves conformability and enhances the range of comfortable movement of the foot and ankle.

Figure 2:
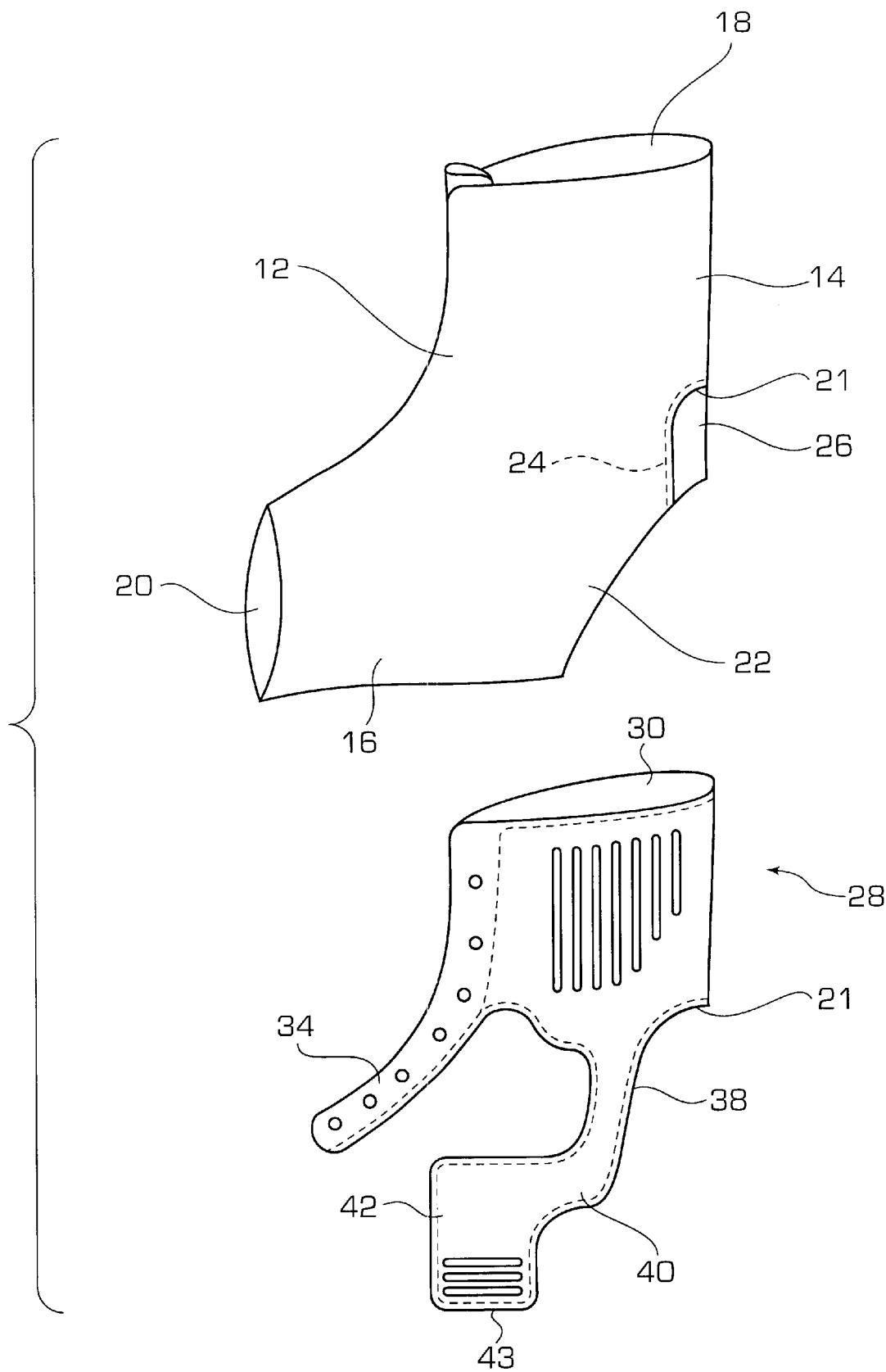
FIG. 2 shows an exploded left side elevational view of the soft support sock, removed from its surrounding formed plastic, closed-cell foam shell.
Figure 4:
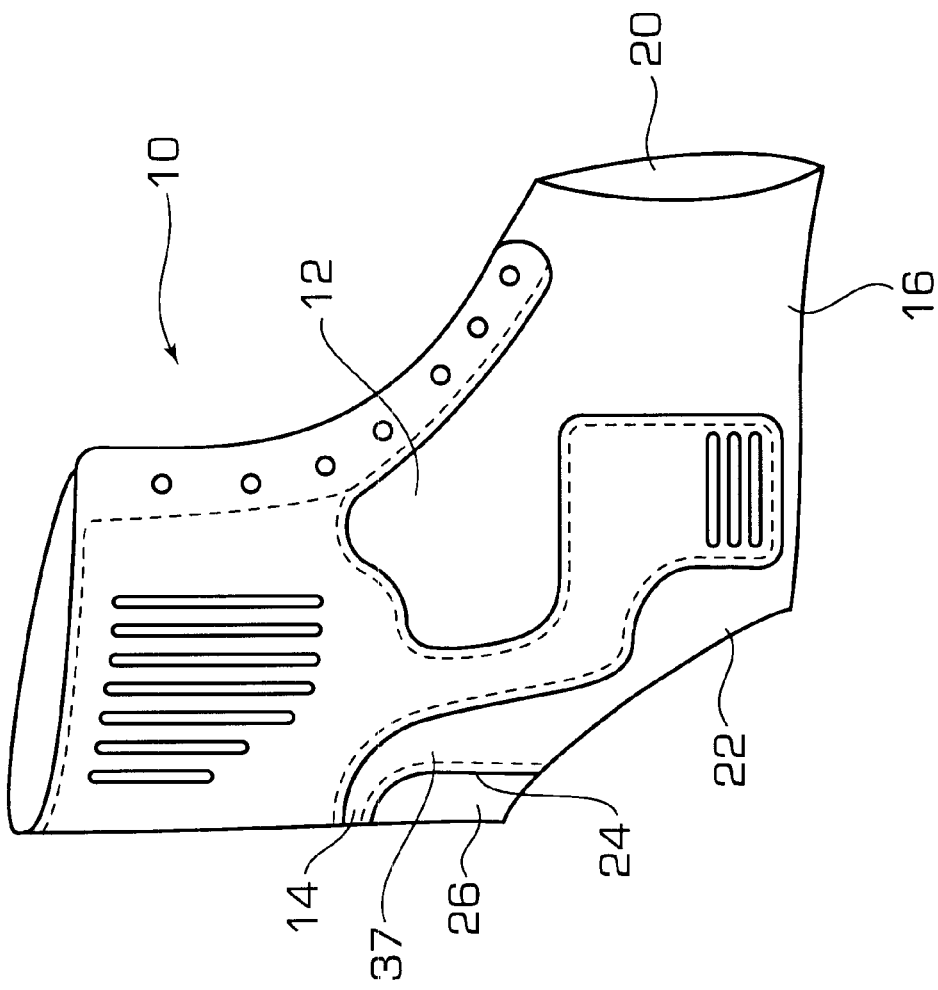
FIG. 4 is a right elevation of the ankle support of FIG. 1, without the straps.

Referring to the assembled form of the ankle support illustrated in FIGS. 1 and 4, it will be seen that the soft brace sleeve 12, shown in the upper half of the exploded view of FIG. 2, is held within a skeletal molded foam shell 28, shown in the lower half of FIG. 2. The pre-molding, pre-sewing, soft foam shell blank for forming this shell is illustrated at 23 in FIG. 5. As seen in that figure, the shell blank is cut to the final shell shape, but is in an initial flat configuration.

Figure 6:
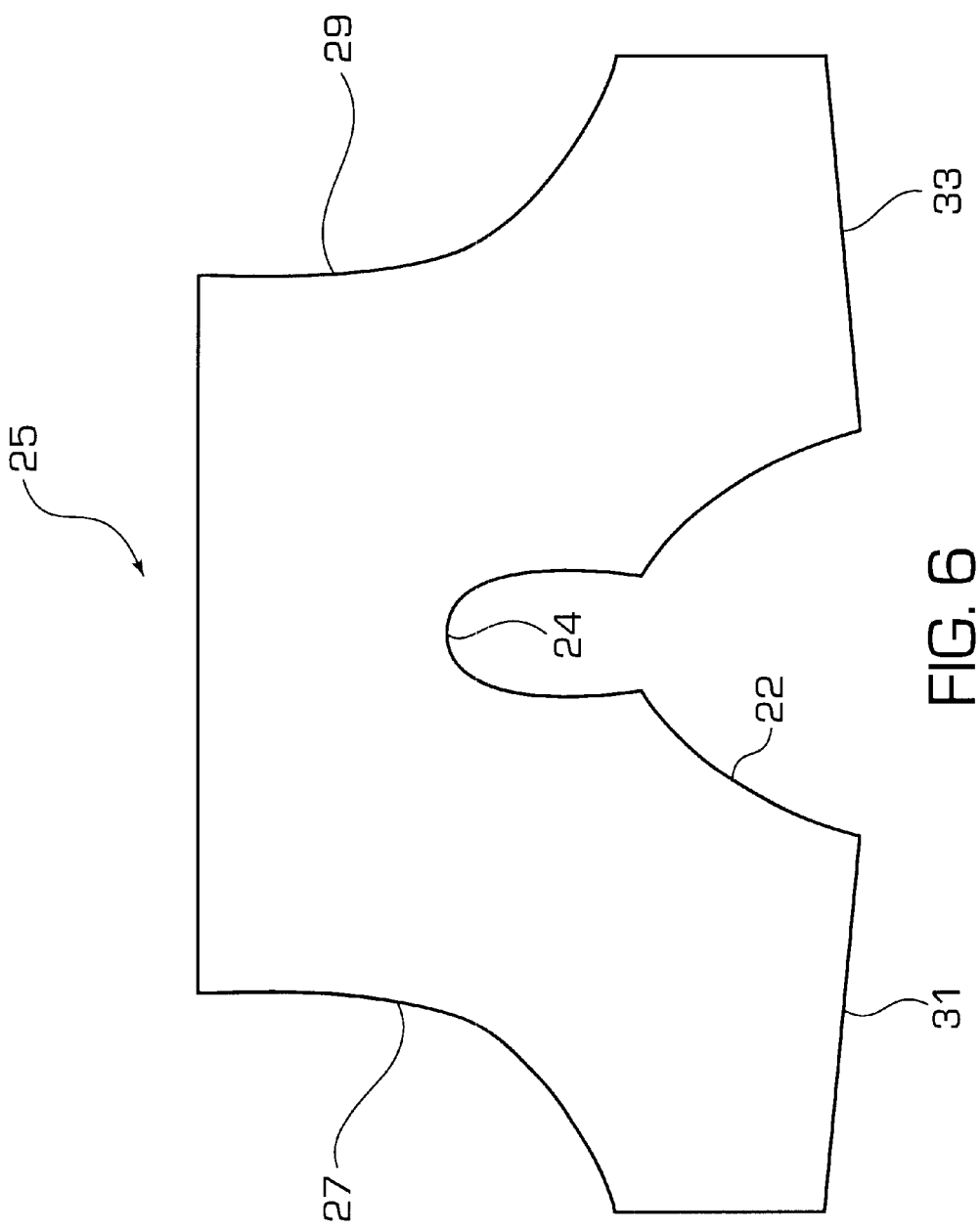
FIG. 6 is a layout plan view of the soft sleeve blank disposed in a flat position, prior to sewing and forming.

The pre-molding, pre-sewing blank for the soft support sleeve 12 is illustrated at 25 in FIG. 6. As seen in that figure, the soft support sleeve blank is cut to its final shape but is in an initial flat configuration. It will be seen that this configuration is generally rectangular, with symmetrical left and right arcuate upper cutouts defined by edges 27 and 29. These edges 27 and 29 will be joined to form a seam which will be generally centered beneath the laced edges of the shell. The lower edges 31 and 33 of the generally rectangular soft support sleeve blank 25 have centrally disposed arcuate cutouts therebetween. These cutouts are defined by the edges 22 and 24. The edge 22 will define the heel cutout in the assembled ankle brace, while the edge 24 will define the cutout for the fabric insert 26.

In fabricating the ankle support, the material for forming the shell 28 is first prepared by creating a sheet of laminated composite material. The composite material preferably comprises a flat sheet of a compressible heat formable closed cell foam. This soft foam sheet is sandwiched between surface sheets of fabric of nylon or the like. The fabric of the surface sheets is not critical and may be woven vinyl. Other fabrics having similar softness and wear characteristics are acceptable. The two sheets of fabric are adhesively or otherwise attached to the sheet foam. The foam may be comprised of any of a number of suitable synthetic materials, such as polypropylene, urethane, polyurethane, olefin, polyolefin, and similar materials. Preferably the foam may be molded at a low temperature not exceeding 200 degrees F. One example of such a material is a polyolefin film marketed under the trademark VOLARA. VOLARA may be obtained from the Voltech division of Sakisui American Corporation located in Lawrence, Mass. 01843. Other of the foregoing resins may be molded at temperatures not exceeding substantially 320 degrees F.

The sheet of composite fabric-foam-fabric laminate is next clipper cut, die cut, or otherwise cut to the desired skeletal shell shape to create a flat uncompressed shell blank.

Figure 5:
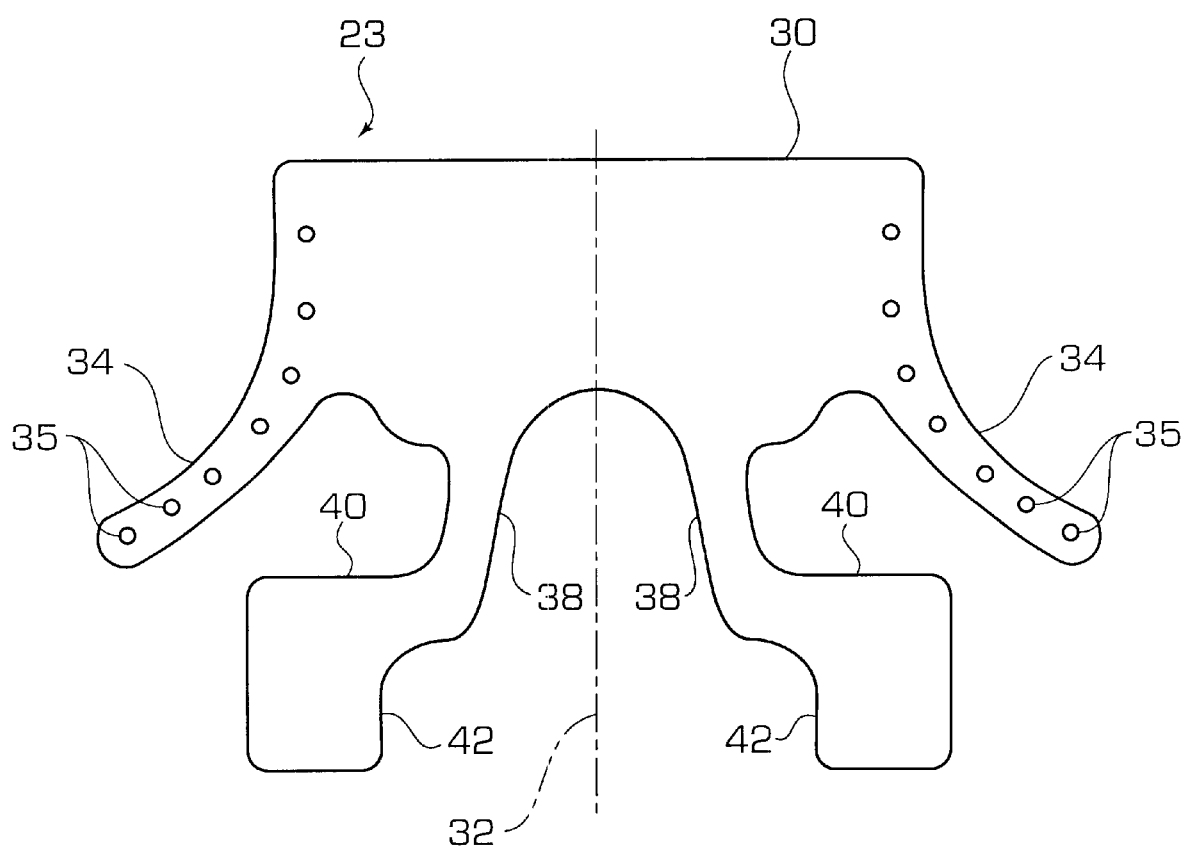
FIG. 5 is a layout plan view of the low temperature, formable plastic, closed-cell foam shell blank for the device of FIG. 1, prior to forming.

Such a blank is shown in its flat configuration at 23 in FIG. 5. In that figure it will be seen that the shell blank is cut to a symmetrical skeletal configuration comprising an upper portion 30 that forms a collar for encircling the leg of a wearer above the ankle joint, as seen in FIGS. 1 and 4. The collar is relatively wide in relation to the widths of the depending stiffening fingers 38.

Referring again to the flat configuration of the shell blank 23 in FIG. 5, according to one embodiment of the invention, the upper collar portion 30 has depending therefrom outer arcuate lacing fingers 34. It will be seen that, in this embodiment of the invention, the cut shell blank is symmetrical about a vertical centerline shown at 32. The outer edges of the lacing fingers 34 are provided with lace apertures 35. The lace apertures 35 receive laces (not shown) to adjust and tighten not only the shell but also the underlying sock on the ankle and foot of a wearer. It will be understood that speed lacing hooks may be substituted in whole or in part for the lacing apertures. Other fastening means, such as hook and loop fasteners, also may be used.

According to an alternate embodiment, the outer lacing fingers 34 do not depend from the collar 30. Referring to FIG. 9 showing this embodiment, it will be seen that separate apertured lacing strips 36 are sewn to the underlying soft support sock in the positions formerly occupied by the lower ends of the lacing fingers 34.

Referring again to the shell blank shown in FIG. 5, a pair of inner stiffener fingers 38 depend from the collar 30 of the shell blank substantially equidistant from the vertical shell certerline 32. The stiffener fingers 38 terminate in generally horizontal support arms 40 which carry downwardly extending support members 42. The downwardly extending support members 42 are wider than the depending inner fingers 38. The combined fingers 38, horizontal support arms 40, and support members 42, provide a unique J shaped support as seen in FIG. 1 and in the left half of the shell blank in FIG. 5. The finger 38 extends downward from the collar generally around the rear of the center of the ankle bone. The horizontal arm extends forward from the finger 38 generally below the center of the ankle bone. The opposite or right half of the shell blank in FIG. 5 is a reversed version of the J shaped support in the left half side.

According to the invention the collar provides substantial support for the depending appendage which is comprised by the depending finger 38, the generally horizontal arm 40, and the widened depending support member 42. In order to effectuate this support the minimum cross section of the finger 38 is such as to provide the desired flexural stiffness to aid in holding the depending appendage snugly against the foot. This cross section may be obtained by an increase in finger thickness or by molding stiffener elements such as ridges as part of the finger. In like manner the desired inward torsion may be transmitted to the support member 42 via the arm 40. This support force may be assisted by straps presently to be described in further detail.

According to another embodiment of the invention, illustrated in FIG. 10, the shell blank may be provided in an asymmetrical shape. In this embodiment the medial depending finger support is not of the same shape as the previously described lateral support 38, 40, and 42. According to this version of the invention, the medial support is smaller than the lateral support, and comprises a downwardly depending finger 53 having a terminus defined by an outwardly extending, generally horizontal, arm 46. This arrangement recognizes differences in ankle anatomy in the lateral and medial sides and may provide a more comfortable and conforming fit in some circumstances.

Returning to the description of the methodology, the laminated and cut sheet foam shell blank 23, seen in FIG. 5, is sewn to the outer surface of the flat soft support sleeve blank 25, shown in FIG. 6. These seams are shown by broken lines 41, 43, and 45 in FIG. 1. A padded tongue 49 is attached to the flat pre-assembly of the shell and sleeve blanks by sewing or tacking the lower end of the tongue to the lower end of one of the arcuate edges 27 or 29 in FIG. 6. The elastic fabric insert 26 is sewn to the edges of the insert cutout 24 above the heel cutout 22. The seam is shown by the broken line at 37 in FIGS. 1 and 4.

Figure 3:
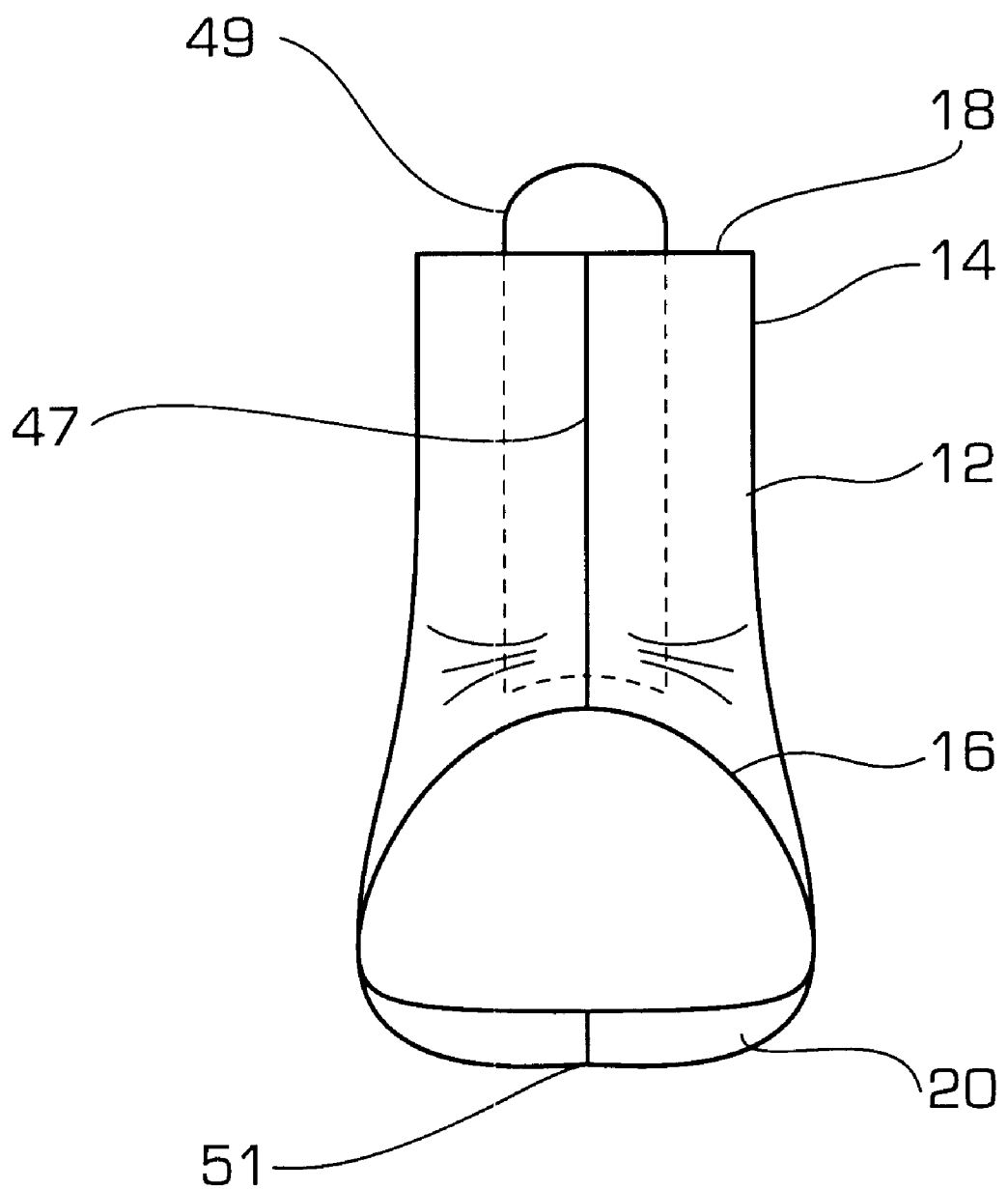
FIG. 3 shows a front elevation of the soft support sock shown in FIG. 2.

The upper arcuate edges 27 and 29 of the soft support sock blank 25 in FIG. 6 are next sewn to one another to form an upper sock seam 47 along the upper surface of the ankle receiving portion 14 of the soft support sock or sleeve 12, as seen in FIGS. 3 and 7. In a similar fashion the lower edges 31 and 33 of the sock blank in FIG. 5 are sewn together to form a central seam 51 along the lower surface of the foot receiving portion 16 of the soft support sock or sleeve 12, as seen in FIG. 3. The sleeve is now in the general configuration shown in FIGS. 2 and 3. Since the shell is now sewn to the outer surface of the sleeve, it too is in the same general configuration. However, the shell has not yet been molded and thus is still soft.

The combined soft support sleeve and its attached and surrounding shell blank are now mounted on a male mold for molding and forming between conventional male and female mold portions. The composite outer shell and inner sleeve assembly is then subjected to selective compression, heat molding, and forming into the desired high topped shoe-like form. As previously stated, the molding is preferably at a low temperature not exceeding 320 degrees F. It is in the nature of the closed cell foam of which the shell is formed that it will retain its compression and heat formed shape after the heat and pressure are removed. The sock or sleeve is unaffected by the molding and retains it softness.

While the pre-forming foam shell blank in FIG. 5 is of a uniform thickness, the formed shell may have a thickness which varies in different portions thereof. In this manner it is possible to vary the degree of support at different portions of the joint being supported. To this end, the female mold is configured, and the compression is applied during the molding step to provide the desired shell thickness and cross section in the various shell elements. Thus the stiffener fingers 38 may be thickened or provided with one or more outer ridges to provide the desired cross section. Also on the outer surface of the molded shell, vertical stiffening ridges 44 may be provided on the collar, best seen in FIG. 1. The ridges 44 may be provided on the molded shell collar in two groups disposed to be positioned on opposite medial and lateral sides of the ankle of a wearer. The ridges in each group are substantially parallel to one another and of varying lengths which are longest substantially directly above the ankle.

According to one embodiment of the invention, one or more of these ridges from each group may extend down onto the depending stiffener fingers 38. Further, horizontal ridges may be provided on the outer surfaces of the widened support members 42, as shown at 55 in FIG. 1. The ridges provide flexible stiffening without the aforementioned disadvantages of rigid stays. Indeed, the formed molded shell itself performs an improved flexible stiffening function for the composite molded foam soft appliance ankle support.

In addition to these ridges, the surfaces of the support members 42 may be provided with medial and lateral outwardly extending protrusions indicated at 57 in FIG. 1.

These protrusions, which are concave on the inside, aid in the ankle cradling function of the J shaped supports.

Referring to FIGS. 1, 7, 8 and 9, the ankle support 10 is provided with support straps 60 and 62. These may be attached to the rear of the collar 30 at 50. In one form the two straps may be provided as a single elongated strap with its midpoint sewn or adhered to the rear of the collar at 50, to effectively form the two straps 60 and 62. These straps provide FIG. 8 support from the outer surface of the molded foam shell.

In use, each of the straps 60 and 62 is wrapped diagonally downwards and forwards as seen in FIGS. 7 and 8, across the top of the foot, down under the metatarsal region of the foot and upwards and diagonally across the top of the foot, and around to the area of attachment to the collar of the shell. Strips of hook and loop fastening material 52, 54, 56, and 58 are provided on the insides and outsides of the straps. The straps are fastened to themselves and/or to one another by bringing the hook and loop strips into engaging relationship. By providing sufficient length to the hook and loop fastening strips a large degree of adjustability may be provided.

It should be noted that the downwardly extending support members 42 on opposite medial and lateral sides of the ankle and foot are separate and distinct. That is, they are not joined beneath the foot, and do not create a rigid stirrup type of ankle and foot confinement. The straps 60 and 62, which provide foot support, are adjustable and provide a wide range of adjustability. One of the functions served by these straps in the device of the invention is to hold the arms 42 snugly to the sides of the foot. This aids in affording adjustability to the support which would otherwise be provided by the dependages and collar.

It will be readily seen by one of ordinary skill in the art that the present invention fulfills the objects and objectives set forth above. After reading the foregoing specification, one of ordinary skill will be able to effect various changes, substitutions of equivalents and to vary other aspects of the invention as broadly disclosed herein. It is therefore intended that the protection granted hereon be limited only by the definition contained in the appended claims and equivalents thereof.

What is claimed is:

1. An ankle support comprising:
   a soft fabric support sock comprising a closed tubular sleeve having an open top for foot insertion, an open heel for heel protrusion, and an open toe for toe protrusion, said sock substantially surrounding the above ankle lower leg, ankle, and foot of a wearer;
   a skeletal shell of low-temperature molded semi-rigid foam sewn to the outer surface of said sock with a sewing seam extending substantially around the periphery of said skeletal shell,
   said shell forming a molded and semi-rigid circumferential collar extending substantially but not completely around said top of said sock above the ankle of a wearer, said collar having upper and lower edges, said upper edge being substantially coterminous with said open top of said sock and said lower edge being spaced above the ankle of a wearer, said upper and lower collar edges terminating in substantially vertical collar end edges adapted to be adjustably secured about the above ankle leg of a wearer;
   said collar having spaced integral medial and lateral elongated stiffener fingers of said molded semi-rigid foam depending downwardly from said lower edge of said collar;
   at least one of said elongated stiffener fingers extending downwardly toward and at least partially around the ankle of a wearer, said at least one stiffener finger having at its lower distal end an enlarged extension extending forward beneath the ankle of a wearer;
   said collar having a vertical width along the above ankle leg of a wearer substantially greater than the horizontal width of said depending stiffener fingers so as to urge said at least one of said stiffener fingers toward the ankle and side of the foot of a wearer.

2. An ankle support according to claim 1 wherein said collar has additional spaced depending fingers, said additional fingers depending from said lower and end edges of said collar and having lace securements for receiving laces to tighten said ankle support on a wearer.

3. An ankle support according to claim 1 including a strap encircling at least said enlarged extension of said stiffener finger beneath the ankle of the wearer and holding it in its support position.

4. An ankle support according to claim 1 wherein said collar has extending from its outer surface one or more elongated stiffener ridges extending generally in parallel to said elongated stiffener fingers depending therefrom.

5. An ankle support according to claim 1 wherein said collar has a width several times the width of said depending fingers.

6. An ankle support comprising:
   a soft fabric support sock comprising a closed tubular sleeve having an open top for foot insertion, an open heel for heel protrusion, and an open toe for toe protrusion, said sock substantially surrounding the above ankle lower leg, ankle, and foot of a wearer;
   a skeletal shell of low-temperature molded semi-rigid foam sewn to the outer surface of said sock with a sewing seam extending substantially around the periphery of said skeletal shell,
   said shell forming a molded and semi-rigid circumferential collar extending substantially but not completely around said top of said sock above the ankle of a wearer, said collar having upper and lower edges, said upper edge being substantially coterminous with said open top of said sock and said lower edge being spaced above the ankle of a wearer, said upper and lower collar edges terminating in substantially vertical collar end edges adapted to be adjustably secured about the above ankle leg of a wearer, said seam being spaced inwardly of said collar end edges so that said end edges are free of said underlying soft fabric support sock;
   said collar having spaced integral medial and lateral elongated stiffener fingers of said molded semi-rigid foam depending downwardly from said lower edge of said collar;
   at least one of said elongated stiffener fingers extending downwardly toward and at least partially around the ankle of a wearer, said at least one stiffener finger having at its lower distal end an enlarged extension extending forward beneath the ankle of a wearer;
   said collar having a vertical width along the above ankle leg of a wearer several times the horizontal width of said depending stiffener fingers so as to urge said at least one of said stiffener fingers toward the ankle and side of the foot of a wearer;
   said collar having protruding from its outer surface elongated stiffener ridges extending generally in parallel to said elongated stiffener fingers depending therefrom, at least one of said stiffener ridges extending from the surface of said collar onto and along the surface of said stiffener finger having said enlarged extension;

said collar having additional spaced depending fingers, said additional fingers depending from said lower and end edges of said collar and having end edges being substantially co-linear with said end edges of said collar, and having lace securements adjacent said additional finger end edges for receiving laces to tighten said ankle support on a wearer; and a tongue disposed between said soft fabric support sock and said end edges of said collar and said end edges of said additional fingers.

7. A method for making an ankle support comprising:

cutting a soft fabric to form a flat blank for a soft tubular orthopedic sock having an open top, heel, and toe, said soft fabric blank being of a generally rectangular configuration having an upper edge, side edges, and lower edges substantially parallel to said upper edge, said blank having symmetrical arcuate cutouts at its upper corners forming arcuate edges joining said upper edge and said side edges;

cutting a sheet of low temperature moldable, closed cell soft synthetic foam having at least one surface laminated to a soft fabric into a skeletal configuration to form a flat blank for a unitary molded semi-rigid shell;

said shell blank having a substantially linear upper edge and an intermediate lower edge generally parallel to said upper edge to form a collar between said upper and intermediate edges, the distance between said upper and intermediate collar edges being less than half of the distance between said upper and lower edges of said sock blank, said collar having spaced integral medial and lateral elongated stiffener fingers of said foam depending from said intermediate edge of said collar substantially normal thereto;

at least one of said stiffener fingers having at its distal end an extension extending away from a vertical centerline of said shell blank, said extension having a lower edge spaced from said lower edges of said sock blank;

assembling said shell blank with said sock blank so that said upper edges of said shell and sock blanks are substantially coterminous;

sewing said skeletal laminated foam shell blank to said soft fabric sock blank to form a seam along said coterminous upper edges of said blanks and to form a seam along the peripheries of said stiffener fingers;

sewing said lower edges of said sock blank to one another and sewing said arcuate edges of said sock blank to one another to form said tubular sock having said open top, heel, and toe;

mounting said sewn sock and surrounding skeletal shell blanks on a male mold, and molding said sock and shell blank assembly under low temperature heat and pressure to form said shell foam into a semi rigid shell around said soft fabric sock.

8. A method according to claim 7 wherein said molding forms areas of different thickness in said skeletal shell defining areas of said shell having different degrees of semi-rigidity.

9. A method according to claim 7 wherein said molding forms stiffening ridges on the outer surfaces of said molded shell.

10. A method according to claim 7 wherein said distance between said upper and intermediate edges of said collar is several times the width of said stiffener fingers extending substantially normal thereto.

* * * * *